(12) United States Patent
Vavvas et al.

(10) Patent No.: US 11,744,817 B2
(45) Date of Patent: *Sep. 5, 2023

(54) HIGH-DOSE STATINS FOR AGE-RELATED MACULAR DEGENERATION

(71) Applicant: MASSACHUSETTS EYE AND EAR INFIRMARY, Boston, MA (US)

(72) Inventors: Demetrios Vavvas, Boston, MA (US); Joan W Miller, Boston, MA (US)

(73) Assignee: MASSACHUSETTS EYE AND EAR INFIRMARY, Boston, MA (US)

(*) Notice: Subject to any disclaimer, the term of this patent is extended or adjusted under 35 U.S.C. 154(b) by 186 days.

This patent is subject to a terminal disclaimer.

(21) Appl. No.: 17/108,065

(22) Filed: Dec. 1, 2020

(65) Prior Publication Data

US 2021/0077457 A1 Mar. 18, 2021

Related U.S. Application Data

(62) Division of application No. 15/768,367, filed as application No. PCT/US2016/056987 on Oct. 14, 2016, now Pat. No. 11,331,295.

(Continued)

(51) Int. Cl.
*A61K 31/22* (2006.01)
*A61P 27/02* (2006.01)
(Continued)

(52) U.S. Cl.
CPC ............ *A61K 31/22* (2013.01); *A61K 31/366* (2013.01); *A61K 31/395* (2013.01); *A61K 31/40* (2013.01);
(Continued)

(58) Field of Classification Search
CPC ...... A61K 31/22; A61K 31/395; A61K 31/40; A61K 31/404; A61K 31/4418;
(Continued)

(56) References Cited

U.S. PATENT DOCUMENTS

2003/0065020 A1 4/2003 Gale et al.
2005/0250745 A1* 11/2005 Seddon ............. G01N 33/6869
436/86

(Continued)

FOREIGN PATENT DOCUMENTS

WO 2003075741 9/2003
WO 2005083430 9/2005
(Continued)

OTHER PUBLICATIONS

Dunbar, Richard, et al., "Effects of omega-3 carboxylic acids on lipoprotein particles and other cardiovascular risk markers in high-risk statin-treated patients with residual hypertriglyceridemia: a randomized, controlled, double-blind trial," Lipids in Health and Disease, (2015).

(Continued)

*Primary Examiner* — Savitha M Rao
*Assistant Examiner* — Andrew P Lee
(74) *Attorney, Agent, or Firm* — Robert C. Netter, Jr.; Dann, Dorfman, Herrell & Skillman

(57) ABSTRACT

Methods of using a high-dose statin for treatment of AMD in a patient can be used to regress drusen and/or drusenoid pigment epithelial detachments (PEDs), to prevent atrophy of the RPE and/or one or more photoreceptors, to prevent vision loss and/or improve visual acuity, and/or to prevent progression from dry AMD to wet AMD.

21 Claims, 11 Drawing Sheets

Related U.S. Application Data

(60) Provisional application No. 62/241,522, filed on Oct. 14, 2015.

(51) Int. Cl.
| | | |
|---|---|---|
| *A61P 27/00* | (2006.01) | |
| *A61K 31/366* | (2006.01) | |
| *A61K 31/395* | (2006.01) | |
| *A61K 31/404* | (2006.01) | |
| *A61K 31/4418* | (2006.01) | |
| *A61K 31/47* | (2006.01) | |
| *A61K 31/505* | (2006.01) | |
| *A61K 31/40* | (2006.01) | |

(52) U.S. Cl.
CPC ........ *A61K 31/404* (2013.01); *A61K 31/4418* (2013.01); *A61K 31/47* (2013.01); *A61K 31/505* (2013.01); *A61P 27/00* (2018.01); *A61P 27/02* (2018.01)

(58) Field of Classification Search
CPC .... A61K 31/47; A61K 31/505; A61K 31/366; A61P 27/00; A61P 27/02
See application file for complete search history.

(56) References Cited

U.S. PATENT DOCUMENTS

| | | |
|---|---|---|
| 2011/0020337 A1 | 1/2011 | Glabe et al. |
| 2012/0156202 A1 | 6/2012 | Shantha et al. |

FOREIGN PATENT DOCUMENTS

| | | |
|---|---|---|
| WO | 2008006535 | 1/2008 |
| WO | 2009023411 | 2/2009 |
| WO | 20150350002 | 3/2015 |
| WO | 2016009430 | 1/2016 |
| WO | 2016018665 | 2/2016 |

OTHER PUBLICATIONS

Gehlbach, Peter, et al., "Stains for age-related macular degeneration" Cochrane Database Syst Rev. Author Manuscript, PMC, Feb. 11, 2016.
Hall, Nigel F., et al., "Risk of macular degeneration in users of statins: cross sectional study," BMJ, vol. 323, pp. 375-376, Aug. 18, 2001.
McGwin, G., et al., "The association between statin use and age related maculopathy," Br J Ophthalmol, pp. 1121-1125, 2003.
Barbosa, et al., "Age-related macular degeneration and protective effect of HMG Co-A reuctase inhibitors (statins): results from the National Health and Nutrition Examination Survey 2005-2008," Eye Clinical Study, pp. 472-480, Feb. 7, 2014.
Guymer, Robyn H., et. al, "Proof of Concept, Randomized, Placebo-Controlled Study of the Effect of Simvastatin on the Course of Age-Related Macular Degeneration," PLOS One, vol. 8, Issue 12, Dec. 31, 2013.
Copenheaver, Blaine R., "PCT International Search Report," Dec. 1, 2017.
Martyn, et al., "Could stains prevent age-related macular degeneration?" Expert Opinion on Pharmacotherapy vol. 3, No. 7, Jul. 1, 2020.
Venturini, Francesca, "European Search Report—Europe App No. 16856248.6" dated May 22, 2019.
Kjekshus, J., et al., "Rosuvastatin in Older Patients with Systolic Heart Failure" N. Engl. J. Med. (2007) 357:2248-61.
Ridker, P.M., et al., "Rosuvastatin to Prevent Vascular Events in Men and Women with Elevated C-Reactive Protein" N. Engl. J. Med. (2008) 359:2195-207.
Gehlbach, P., et al., "Statins for age-related macular degeneration (Review)" Cochrane Database of Systematic Reviews (2016) 8:CD006927, pp. 1-33.
Guymer, R.H., et al., "Proof of Concept, Randomized, Placebo-Controlled Study of the Effect of Simvastatin on the Course of Age-Related Macular Degeneration" PLoS ONE (2013) 8(12): e83759.
Nikipedia, "Salicylate poisoning", obtained at https://en.wikipedia.org/wiki/Salicylate_poisoning.
Gehlbach, P., et al., "Statins for age-related macular degeneration" Cochrane Database of Systematic Reviews (Feb. 11, 2015) 2:CD006927, pp. 1-41, available at doi.org/10.1002/14651858.CD006927.pub4.
Vavvas, et al., "Regression of Some High-risk Features of Age-related Macular Degeneration (AMD) in Patients Receiving Intensive Statin Treatment" EBioMedicine (2016) 5:198-203.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss: AREDS Report No. 8" Arch Ophthalmol. (2001) 119(10):1417-1436.
Age-Related Eye Disease Study 2 Research Group, "Lutein + Zeaxthine and Omega-3 Fatty Acids for Age-Related Macular Degeneration" JAMA (2013) 309:2005-2015.
Bayer, A.U., "Junction Study: SD-OCT Shows Shrinking And Disappearing Of Drusen In Nonexudative AMD Eyes Treated With AREDS 2 Supplements Plus A Complex Containing The Natural Compounds Curcumin, Omega 3 DHA/EPA and Phospholipids" Investigative Ophthalmology & Visual Science (2012) 53:448.
Virgili, et al., "Laser treatment of drusen to prevent progression to advanced age-related macular degeneration (Review)" Cochrane Database of Systematic Reviews (2015) 10:CD006537.
Maguire, M.G., "Drusen Volume as a Study Endpoint" Opthalmology (2012) 119:150-1502.
Smeeth, et al., "A case control study of age related macular degeneration and use of statins" Br J Ophthalmol (2005) 89:1171-1175.
Tian, et al., "Atorvastatin Promotes Phagocytosis and Attenuates Pro-Inflammatory Response in Human Retinal Pigment Epithelial Cells" Scientific Reports (2017) 7:2329.
Mast, et al., "Retinal Cholesterol Content Is Reduced in Simvastatin-Treated Mice Due to Inhibited Local Biosynthesis Albeit Increased Uptake of Serum Cholesterol" Drug Metab Dispos (2018) 46:1528-1537.

\* cited by examiner

HIGH-DOSE STATINS FOR AGE-RELATED MACULAR DEGENERATION

TECHNICAL FIELD

This disclosure relates to materials and methods of using high-dose statins for the treatment of age-related macular degeneration.

BACKGROUND

Age-related macular degeneration (AMD) is a multifactorial heterogeneous disease, with at least 100 different at-risk genes reported in the literature and with several different phenotypes, including types and size of drusen (Miller, 2013 *Am J Ophthalmol* 155(1):1-35.e13). AMD is the leading cause of irreversible vision loss in the developed world, and is broadly classified into the atrophic or "dry" form and the neovascular or "wet" form.

SUMMARY

Provided herein are materials and methods of using high-dose statins for the treatment of age-related macular degeneration. There are effective antiangiogenic treatments for neovascular AMD, but effective treatments are lacking for the more prevalent dry form.

In some embodiments, methods provided herein include a method of treating age-related macular degeneration (AMD) in a patient. The method includes identifying the patient as having AMD and administering to the patient a high-dose statin. The high-dose statin is effective to cause a regression of a drusen in the patient. The method can include monitoring the patient for drusen regression. Drusen regression can be a reduced drusen size of at least 85% or complete regression.

In some embodiments, methods provided herein include a method of treating age-related macular degeneration (AMD) in a patient. The method includes identifying the patient as having AMD and administering to the patient a high-dose statin. The high-dose statin is effective to prevent atrophy of a retinal pigmented epithelium (RPE) in the patient.

In some embodiments, methods provided herein include a method of treating age-related macular degeneration (AMD) in a patient. The method includes identifying the patient as having AMD and administering to the patient a high-dose statin. The high-dose statin is effective to prevent atrophy of one or more photoreceptors in the patient.

In some embodiments, methods provided herein include a method of treating age-related macular degeneration (AMD) in a patient. The method includes identifying the patient as having AMD and administering to the patient a high-dose statin. The high-dose statin is effective to prevent geographic atrophy.

In some embodiments, methods provided herein include a method of treating age-related macular degeneration (AMD) in a patient. The method includes identifying the patient as having AMD and administering to the patient a high-dose statin. The high-dose statin, is effective to prevent vision loss in the patient.

In some embodiments, methods provided herein include a method of treating age-related macular degeneration (AMD) in a patient. The method includes identifying the patient as having AMD and administering to the patient a high-dose statin, wherein the high-dose statin is effective to improve visual acuity in the patient. Visual acuity can be improved by at least 3 letters. Visual acuity can be improved by at least 12 letters.

In some embodiments, methods provided herein include a method of treating age-related macular degeneration (AMD) in a patient. The method includes identifying the patient as having AMD and administering to the patient a high-dose statin. The high-dose statin is effective to preventing progression to wet AMD in the patient.

In any of the methods provided herein, the patient can be mammal. For example, the patient can be a human. In some embodiments, the human has large, soft drusen and/or drusenoid PEDs in one or both eyes.

In any of the methods provided herein, the high-dose statin can be administered for at least 12 months. In some embodiments, the high-dose statin can be administered for at least 36 months.

In any of the methods provided herein, the high-dose statin can be administered orally.

In any of the methods provided herein, the high-dose statin can be selected from the group consisting of atorvastatin, cerivastatin, fluvastatin, lovastatin, pitavastatin, pravastatin, rosuvastatin, simvastatin, and analogs thereof. In some embodiments, the high-dose statin can include a dose equivalent of at least 40 mg atorvastatin. The high-dose statin can be at least 40 mg atorvastatin. In some embodiments, the high-dose statin can include a dose equivalent of at least 80 mg atorvastatin. The high-dose statin can be at least 80 mg atorvastatin.

In any of the methods provided herein, the method can further include administering an additional therapeutic agent selected from the group consisting of an anti-inflammatory agent, an anti-angiogenic agent, an anti-oxidative agent, an omega-3 fatty acid, and a vitamin/mineral.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
FIG. 1 is a series of fundoscopy images. At the beginning of the trial, bilateral extensive confluent large soft drusen and pigmentary alterations are seen (top row). Administration of Age-Related Eye Disease Study (AREDS) supplementation did not affect drusen (middle row). Six months after 80 mg atorvastatin, the disappearance of the drusen is seen (bottom row).

Age-related macular degeneration (AMD) is the leading cause of irreversible vision loss in adults in the Western world (Wong et al., 2014 *Lancet Glob Health* 2(2):e106-16).

AMD is broadly classified into two types. The atrophic or "dry" form is the most prevalent, characterized by accumulation of extracellular deposits, termed drusen, between the retinal pigmented epithelium (RPE) and the choroid. Progression to advanced AMD may involve, for example, atrophy of the RPE and/or one or more photoreceptors, and/or abnormal choroidal neovascularization (neovascular or "wet" AMD). Though it is less prevalent than the dry form, neovascular AMD is associated with rapid vision loss. However, despite effective antiangiogenic treatments for neovascular AMD, effective treatments are lacking for the more prevalent dry form.

Provided herein are methods of using a high-dose statin for treatment of AMD in a patient. For example, the methods provided can be used to regress drusen (e.g., soft drusen), to regress drusenoid pigment epithelial detachments (PEDs), to prevent atrophy of the RPE, to prevent atrophy of one or more photoreceptors, to prevent vision loss, to improve visual acuity, and/or to prevent progression from dry AMD to wet AMD.

Drusen

One of the hallmark manifestations of dry AMD is the accumulation of drusen, the components of which are derived from local tissues (RPE/retina) and from the circulation (Curcio et al., 2011 *Br J Ophthalmol* 95(12):1638-45; Wu et al., 2010 *J Neurochem* 114(6):1734-44). Also associated with AMD are drusenoid pigment epithelial detachments (PEDs), in which the retinal pigment epithelium separates from the underlying Bruch's membrane due to the presence of one or more drusen.

Drusen can be hard drusen or soft drusen. "Hard" drusen are small, distinct and far away from one another, and may not cause vision problems for a long time, if at all. "Soft" drusen have poorly defined edges, are large, and cluster closer together. Lipids are a major constituent of drusen, with esterified cholesterol (EC), unesterified cholesterol (UC), and phosphatidyl choline constituting 40% of the volume of hard drusen. Soft drusen are more fragile than hard drusen and oily upon dissection, consistent with high lipid constitution. The presence of soft drusen is one of the major risk factors for the subsequent development of advanced dry or wet AMD. In some embodiments, the drusen treated by a method described herein are soft drusen.

Statins

The methods described herein include administration of high-dose statins. Statins (or HMG-CoA reductase inhibitors) are a class of cholesterol lowering drugs that are similar in structure to HMG-CoA, shown below:

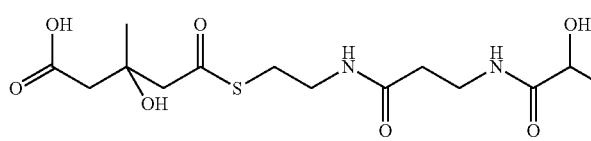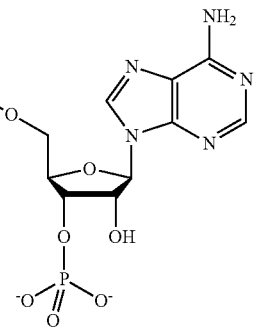

Statins inhibit the enzyme HMG-CoA reductase by competitively binding to HMG-CoA reductase in the HMG-CoA active site. Any statin may be used in the methods described herein. Non-limiting examples of statins include: atorvastatin (LIPITOR®), cerivastatin, fluvastatin (LESCOL®), lovastatin (MEVACOR®, ALTOCOR™), pitavastatin (UVALO®), pravastatin (PRAVACHOL®, SELEKTINE®), rosuvastatin (CRESTOR®) simvastatin (ZOCOR®), analogs thereof, and combinations thereof. In some embodiments, a statin is atorvastatin.

Statins can be either lipophilic or hydrophilic. Lipophilic statins include, for example, atorvastatin, lovastatin, and simvastatin. Hydrophilic statins include, for example, fluvastatin, rosuvastatin, and pravastatin. In some embodiments, a statin is lipophilic (e.g., atorvastatin).

As used herein the term "high-dose" refers to any dose that exceeds than the defined daily dose (DDD) according to the World Health Organization (WHO). The 2015 ATC/DDD Index indicates the DDD as 20 mg for atorvastatin, 0.2 mg for cerivastatin, 60 mg for fluvastatin, 45 mg for lovastatin, 2 mg for pitavastatin, 30 mg for pravastatin, 10 mg for rosuvastatin, and 30 mg for simvastatin (see, e.g., whocc.no/atc_ddd_index/). For example, in embodiments where a statin is atorvastatin (having a DDD of 20 mg), a high-dose of atorvastatin can be at least 40 mg, at least 50 mg, at least 60 mg, at least 70 mg, at least 80 mg, at least 90 mg, or at least 100 mg. In some embodiments, a high-dose statin is at least 80 mg atorvastatin.

In other embodiments, a dose equivalent of high-dose atorvastatin can be used. Equivalent doses of other statins can be easily determined by a skilled person. For example, based on the DDD of the statins, an equivalent dose of 80 mg atorvastatin could be 0.8 mg for cerivastatin, 240 mg for fluvastatin, 180 mg for lovastatin, 8 mg for pitavastatin, 120 mg for pravastatin, 40 mg for rosuvastatin, and 120 mg for simvastatin.

Also provided herein are methods of using maintenance-dose statins. For example, following effective treatment of AMD, the amount of statin administered can be reduced from a high-dose statin to a maintenance-dose statin. As used herein a "maintenance dose" is lower than the high-dose and indicates a dose of statin that is about equal to the DDD according to the WHO of a statin. For example, a maintenance dose of atorvastatin (having a DDD of 20 mg) can be about 15 mg, about 20 mg, about 25 mg, about 30 mg, about 35 mg, about 40 mg, about 45 mg, about 50 mg, about 55 mg, or about 60 mg. In some embodiments, a maintenance-dose statin is about 60 mg atorvastatin. In some embodiments, a maintenance-dose statin is about 40 mg atorvastatin.

In other embodiments, a dose equivalent of maintenance-dose atorvastatin can be used. Equivalent doses of other statins can be easily determined by a skilled person. For example, based on the DDD of the statins, an equivalent maintenance-dose of 40 mg atorvastatin could be 0.4 mg for cerivastatin, 120 mg for fluvastatin, 90 mg for lovastatin, 4 mg for pitavastatin, 60 mg for pravastatin, 20 mg for rosuvastatin, and 60 mg for simvastatin.

Methods of Use

Provided herein are methods of using a high-dose statin for treatment of AMD in a patient. In some embodiments, this disclosure provides methods of regressing drusen (e.g., soft) and/or drusenoid PEDs in a patient. In some embodiments, this disclosure provides methods of preventing (i.e., reducing the risk of) atrophy of the RPE and/or one or more photoreceptors in a patient. In some embodiments, this disclosure provides methods of preventing (i.e., reducing the risk of) vision loss and/or improving visual acuity in a patient. In some embodiments, this disclosure provides methods of preventing (i.e., reducing the risk of) AMD progression (e.g., from dry AMD to wet AMD) in a patient. Methods provided herein can include administering to a patient a high-dose statin as described herein. Methods provided herein can also include subsequent administering to a patient a maintenance-dose statin as described herein. Methods provided herein can also include identifying a patient as having AMD (e.g., dry AMD) or soft drusen, and optionally selecting the patient on the basis that they have AMD or soft drusen. Methods are known in the art to diagnose AMD and drusen in a patient. Methods provided herein can also include monitoring the patient for efficacy of administering to a patient a high-dose statin as described herein (e.g., monitoring the patient for drusen regression, atrophy of the RPE and/or one or more photoreceptors, vision loss and/or visual acuity, AMD progression).

A patient can include both mammals and non-mammals. Non-limiting examples of mammals include, for example, humans, nonhuman primates (e.g. apes and monkeys), cattle, horses, sheep, rats, mice, pigs, and goats. Non-limiting examples of non-mammals include, for example, fish and birds. In some embodiments, a patient is a human. In some embodiments, a patient is a human having AMD with high-risk features for progression (e.g., presence of many large, soft drusen and/or drusenoid PEDs in one or both eyes).

Administration of a high-dose and/or a maintenance-dose statin as described herein to a patient can include administering the statin for a suitable amount of time. For example, a high-dose statin as described herein can be administered to a patient for at least 12 months, at least 15 months, at least 18 months, at least 21 months, at least 24 months, at least 30 months, at least 33 months, at least 36 months, at least 39 months, at least 42 months, at least 45 months, or at least 48 months. In some embodiments, a high-dose and/or a maintenance-dose statin as described herein is administered to a patient for at least 36 months.

Administration of a high-dose and/or a maintenance-dose statin as described herein to a patient can include administering the statin one or more times each day (e.g., once a day, twice a day, three times a day, etc.) provided the total daily amount is in accordance with the daily doses described herein. For example, a high-dose statin (e.g., 80 mg atorvastatin) can be administered once daily at the full high-dose statin, twice a day where the combination of the two administrations total the full high-dose statin, three times a day where the combination of the three administrations total the full high-dose statin, etc. In some embodiments, a high-dose and/or a maintenance-dose statin as described herein is administered to a patient once daily.

A high-dose and/or a maintenance-dose statin described herein can be administered by any route; e.g., intravenous (IV), ocular (e.g., intravitreal, topical drops, or topical ointments), intramuscular, subcutaneous, oral, intranasal, inhalation, transdermal, and parenteral. In some embodiments, a statin described herein is administered orally. In some embodiments, a statin described herein is administered intravitreally.

For oral administration, a high-dose and/or a maintenance-dose statin described herein can be in the form of a pill, tablet, powder, liquid, capsule, or other suitable oral dosage form. Tablets or capsules can be prepared with pharmaceutically acceptable excipients such as binding agents, fillers, lubricants, disintegrants, or wetting agents. Liquid preparations for oral administration can take the form of, for example, solutions, syrups, or suspension, or they can be presented as a dry product for constitution with saline or other suitable liquid vehicle before use.

The specific dose of a high-dose and/or a maintenance-dose statin described herein will, of course, be determined by the particular circumstances of the individual patient including the size, weight, age and sex of the patient, the nature and stage of the disease being treated, the aggressiveness of the disease disorder, and the route of administration of the compound.

A "therapeutically effective amount" of a high-dose statin described herein (e.g., a high-dose atorvastatin) provided herein is typically one which is sufficient to achieve the desired effect (e.g., regressing drusen and/or drusenoid PEDs, reducing the amount immunogenic and/or toxic material, preventing atrophy, preventing vision loss, improving visual acuity, preventing progression, etc.) and may vary according to the nature and severity of the AMD, and the potency of the high-dose statin described herein.

An "effective amount" of a maintenance-dose statin described herein (e.g., a maintenance-dose atorvastatin) provided herein is typically one which is sufficient to prevent any further change in the measured parameter and may vary according to the nature and severity of the AMD, and the potency of the maintenance-dose statin described herein.

"Preventing" as used herein refers to reducing risk of development or progression of a condition in a subject; just as a therapeutic treatment need not cure 100% of subjects or symptoms to be effective and clinically useful, a preventative treatment need not eliminate 100% of all risk of development or progression of the condition in the subject. Thus, a treatment that "prevents" atrophy of the RPE, atrophy of one or more photoreceptors, vision loss, and/or progression from dry AMD to wet AMD is one that reduces the risk in the subject of atrophy of the RPE, atrophy of one or more photoreceptors, vision loss, and/or progression from dry AMD to wet AMD.

Methods of regressing drusen and/or drusenoid PEDs a patient can include administering to a patient a high-dose statin as described herein. Regression of drusen and/or drusenoid PEDs can be assessed by any suitable manner including, for example, ocular examinations such as biomicroscopy, stereoscopic fundus examination (e.g., color fundus photography), macular function assessment, optical coherence tomography (OCT), autofluorescence, and/or angiography (e.g., fluorescein angiography). Administration of a high-dose statin as described herein can be effective to reduce the size of a drusen in the patient relative to a patient with AMD that did not receive a high-dose statin as described herein. For example, drusen regression can be by at least 5%, at least 10% at least 15%, at 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Drusen can be evaluated, for example, by measuring a parameter such as volume, height, diameter, and/or number. Thus, drusen regression can be evaluated by determining a particular parameter of drusen in a patient at a first time point (e.g., prior to administration of a high-dose statin), determining the same parameter in the same patient at a second time point (e.g., after administration of a high-dose statin), and comparing the measured parameter at the first time point and the second time point. A reduction in the measured parameter from the first time point to the second time point is indicative of drusen regression. In some embodiments, administration of a high-dose statin can be effective to reduce drusen by at least 40%. In some embodiments, administration of a high-dose statin as described herein can be effective to cause complete regression (i.e., 100% regression) the drusen. Administration of a maintenance-dose statin as described herein can be effective to prevent drusen from enlarging and/or forming in a patient.

Also associated with AMD are drusenoid pigment epithelial detachments (PEDs), in which the retinal pigment epithelium separates from the underlying Bruch's membrane due to the presence of one or more drusen. Methods of regressing drusenoid PEDs can result in resolution of the drusenoid PED by PED flattening and/or re-attachment to the Bruch's membrane. Resolution of the drusenoid PED can be assessed by any suitable manner including, for example, OCT, angiography (e.g., fluorescein angiography), autofluorescence, and/or macular status. Administration of a high-dose statin as described herein can be effective to regress drusenoid PEDs in the patient relative to a patient with AMD that did not receive a high-dose statin as described herein. Administration of a high-dose statin as described herein can be effective to flatten the PED and/or re-attach the PED to the Bruch's membrane. For example, a PED can be flattened by at least 5%, at least 10% at least 15%, at 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. For example, the separation between a PED and the Bruch's membrane can be reduced by at least 5%, at least 10% at least 15%, at 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. PED can be evaluated for flattening, for example, by measuring a parameter such as volume, height, and/or diameter, and can be evaluated for re-attaching to the Bruch's membrane by, for example, measuring a parameter such as the distance of the separation. Thus, PED flattening and/or re-attachment to the Bruch's membrane can be evaluated by determining a particular parameter of drusen in a patient at a first time point (e.g., prior to administration of a high-dose statin), determining the same parameter in the same patient at a second time point (e.g., after administration of a high-dose statin), and comparing the measured parameter at the first time point and the second time point. A reduction in the measured parameter from the first time point to the second time point is indicative of regression of drusenoid PEDs (e.g., by PED flattening and/or re-attachment to the Bruch's membrane). In some embodiments, the separation between the PED and the Bruch's membrane can be reduced by at least 30%. Administration of a maintenance-dose statin as described herein can be effective to prevent PEDs from enlarging and/or forming in a patient.

Without being bound by theory, it is believed that regressing drusen and/or drusenoid PEDs result from enhances phagocytic function of RPE cells. Phagocytic function can be assessed by any suitable manner including, for example, flow cytometry. Administration of a high-dose statin as described herein can be effective to enhance phagocytic function in RPE cells of the patient relative to a patient with AMD that did not receive a high-dose statin as described herein. For example, the percentage of phagocytic cells can be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Administration of a maintenance-dose statin as described herein can be effective to prevent PEDs from enlarging and/or forming in a patient.

Drusen are known to contain several immunogenic and toxic materials, such as complement (Crabb, 2014 *Cold Spring Harb Perspect Med* 4(7):a017194-4), 7-ketocholesterol (Rodriguez et al., 2014 *Exp Eye Res* 128:151-5), and amyloid (Luibl et al., 2006 *J Clin Invest* 116(2):378-85). Administration of a high-dose statin as described herein can be effective to reduce the amount of immunogenic and/or toxic material in the patient relative to a patient with AMD that did not receive a high-dose statin as described herein. Administration of a maintenance-dose statin as described herein can be effective to prevent an increase in the amount of immunogenic and/or toxic material in a patient.

Methods of preventing atrophy of the RPE and/or one or more photoreceptors in a patient can include administering to a patient a high-dose statin as described herein. The RPE closely interacts with and supplies nutrients to the photoreceptors. Drusen are location between the RPE and its vascular supply, the choriocapillaris. Without being bound by theory, it is possible that drusen deprive the RPE and photoreceptor cells of oxygen and nutrients resulting in atrophy of both the RPE and photoreceptors. Atrophy of both the RPE and photoreceptors is typically referred to as geographic atrophy. Prevention of atrophy can be assessed by any suitable manner including, for example, ocular examinations such as biomicroscopy, stereoscopic fundus examination (e.g., color fundus photography), macular function assessment, OCT, autofluorescence, and/or angiography (e.g., fluorescein angiography). Administration of a high-dose statin as described herein can be effective to reduce the amount of atrophy of the RPE and/or one or more photoreceptors in the patient relative to a patient with AMD that did not receive a high-dose statin as described herein. For example, the amount of atrophy can be reduced by at least 5%, at least 10% at least 15%, at 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Atrophy can be evaluated, for example, by measuring a parameter such as autofluorescence or retinal thickness. Thus, amount of atrophy can be evaluated by determining a particular parameter of drusen in a patient at a first time point (e.g., prior to administration of a high-dose statin), determining the same parameter in the same patient at a second time point (e.g., after administration of a high-dose statin), and comparing the measured parameter at the first time point and the second time point. Maintenance or a reduction in the measured parameter from the first time point to the second time point is indicative of prevention of atrophy (e.g., atrophy of the RPE and/or one or more photoreceptors). In some embodiments, methods provided herein can be used to prevent atrophy of both the RPE and photoreceptors in a patient. Administration of a maintenance-dose statin as described herein can be effective to prevent an increase in the amount of atrophy of the RPE and/or one or more photoreceptors in a patient.

In some embodiments, administration of a high-dose statin as described herein can be effective to cause a complete disappearance (i.e., 100% regression) of the drusen and prevent atrophy of both the RPE and photoreceptors in a patient (i.e., geographic atrophy).

Methods of preventing vision loss and/or improving visual acuity in a patient can include administering to a patient a high-dose statin as described herein. Visual acuity can be assessed by any suitable manner including, for example, determining the smallest letters the patient can read on a standardized chart (e.g., a Snellen chart) or card held about 20 feet away. In some embodiments, methods provided herein can be used to prevent vision loss in a patient. Administration of a high-dose statin as described herein can be effective to prevent vision loss in the patient relative to a patient with AMD that did not receive a high-dose statin as described herein. For example, administration of a high-dose statin as described herein can be effective to prevent vision loss by losing no greater than 5 letters, no greater than 4 letters, no greater than 3 letters, no greater than 2 letters, no greater than 1 letter. In some embodiments, administration of a high-dose statin as described herein is effective to prevent vision loss by losing no greater than 2 letters. In some embodiments, administration of a statin as described herein is effective to prevent vision loss by maintaining visual acuity (i.e., no loss in visual acuity is detectable). Administration of a maintenance-dose statin as described herein can be effective to prevent vision loss in a patient.

In some embodiments, methods provided herein can be used to improve visual acuity in a patient. Administration of a high-dose statin as described herein can be effective to improve visual acuity in the patient relative to a patient with AMD that did not receive a high-dose statin as described herein. For example, administration of a high-dose statin as described herein can be effective to improve visual acuity by at least 2 letters, at least 3 letters, at least 4 letters, at least 5 letters, at least 6 letters, at least 7 letters, at least 8 letters, at least 9 letters, at least 10 letters, at least 11 letters, at least 12 letters, at least 13 letters, at least 14 letters, at least 15 letters. In some embodiments, administration of a high-dose statin as described herein is effective to improve visual acuity by 3 letters. In some embodiments, administration of a high-dose statin as described herein is effective to improve visual acuity by 12 letters.

Methods of preventing AMD progression (e.g., from dry AMD to wet AMD) in a patient can include administering to a patient a high-dose statin as described herein. Prevention of AMD progression can be assessed by any suitable manner including, for example, ocular examinations such as biomicroscopy, tonometry, stereoscopic fundus examination (e.g., color fundus photography), macular function assessment, OCT, and/or angiography (e.g., fluorescein angiography, and OCT based angiography (OCTA)). Administration of a high-dose statin as described herein can be effective to prevent progression to wet AMD in the patient relative to a patient with AMD that did not receive a high-dose statin as described herein. In some embodiments, administration of a high-dose statin as described herein can be effective to prevent progression from dry AMD to wet AMD. Administration of a high-dose statin as described herein can be can be effective to prevent progression to wet AMD. For example, progression to wet AMD may involve, for example, abnormal choroidal neovascularization. For example, administration of a high-dose statin as described herein can be effective to reduce and/or prevent choroidal neovascularization. Progression of AMD can be evaluated by, for example, measuring a parameter such as neovascularization. Thus, progression of AMD evaluated by determining a particular parameter of drusen in a patient at a first time point (e.g., prior to administration of a high-dose statin), determining the same parameter in the same patient at a second time point (e.g., after administration of a high-dose statin), and comparing the measured parameter at the first time point and the second time point. Maintenance or a reduction in the measured parameter from the first time point to the second time point is indicative of the prevention of AMD progression (e.g., from dry AMD to wet AMD).

Methods provided herein can also include administration of an additional therapeutic agent, in addition to the statin. As used herein, an additional therapeutic agent includes any molecule that can have a therapeutic effect on AMD. Examples of therapeutic agents include anti-inflammatory agents (e.g., anti-IL-6 agent, anti-IL-8 agents, aspirin, ibuprofen, and naproxen), anti-angiogenic agents (e.g., anti-VEGF agents, ranibizumab, bevacizumab, acadesine, and AMPK activators), anti-oxidative agents (e.g., vitamin C, vitamin E, vitamin A, glutathione, catalase, etc.), omega-3 fatty acids (e.g., α-linolenic acid (ALA), eicosapentaenoic acid (EPA), and docosahexaenoic acid (DHA)), and vitamins/minerals (e.g., vitamin C, vitamin E, vitamin A, lutein, zeaxanthin, zinc, and copper).

A therapeutic agent described herein can be administered by any route (e.g., intraocular, intravenous (IV), intramuscular, subcutaneous, oral, ocular (e.g. intravitreal, topical drops, or topical ointment), intranasal, inhalation, transdermal, and parenteral), and by any method (e.g., injection, pump (e.g., an implantable pump), etc.). In some embodiments, an active agent described herein is administered orally.

The high-dose statin described herein (e.g., a high-dose atorvastatin) and the therapeutic agent can be administered to the patient independently or administered to the patient simultaneously. In cases where the high-dose statin and the therapeutic agent are administered to the patient simultaneously, the high-dose statin and the therapeutic agent can be a single dosage form or the high-dose statin and the active agent can be separate dosage forms.

Methods provided herein can also include administration of a maintenance dose of a statin. For example, following effective treatment of AMD (e.g., regression of drusen), administration of a high-dose statin as described herein can be replace with administration of a maintenance dose of a statin.

The invention will be further described in the following examples, which do not limit the scope of the invention described in the claims.

EXAMPLES

Example 1: High-Dose Statin for Regression of Drusen and Improvement of Visual Acuity This example, presents the first evidence that treatment with high-dose atorvastatin results in regression of drusen and improvement of visual acuity in patients with AMD with high-risk features for progression.

Methods

A case report and pilot multi-center prospective interventional study were conducted with IRB approval. Inclusion criteria were patients over the age of 50 with diagnosis of AMD and the presence of many large, soft drusen/drusenoid PEDs in both eyes. Exclusion criteria were as follows: presence (or history) of significant geographic atrophy or choroidal neovascularization in either eye; other eye diseases that could reduce visual acuity (except for mild cataract); history of eye surgery (other than cataract extraction); patients currently or recently (within 2 years) on statin therapy at a dose equivalent to atorvastatin 40 mg; history of liver disease, rhabdomyolysis, or allergy to statins; pregnancy or nursing; current use of medications known to interact with statins (e.g., cyclosporine, systemic itraconazole, clarithromycin, HIV protease inhibitors); and elevated transaminases or creatinine kinase at baseline. Pseudophakia was not a reason for exclusion, unless accompanied by significant posterior capsular opacity.

Results

Report of Initial Case

Figure 2:
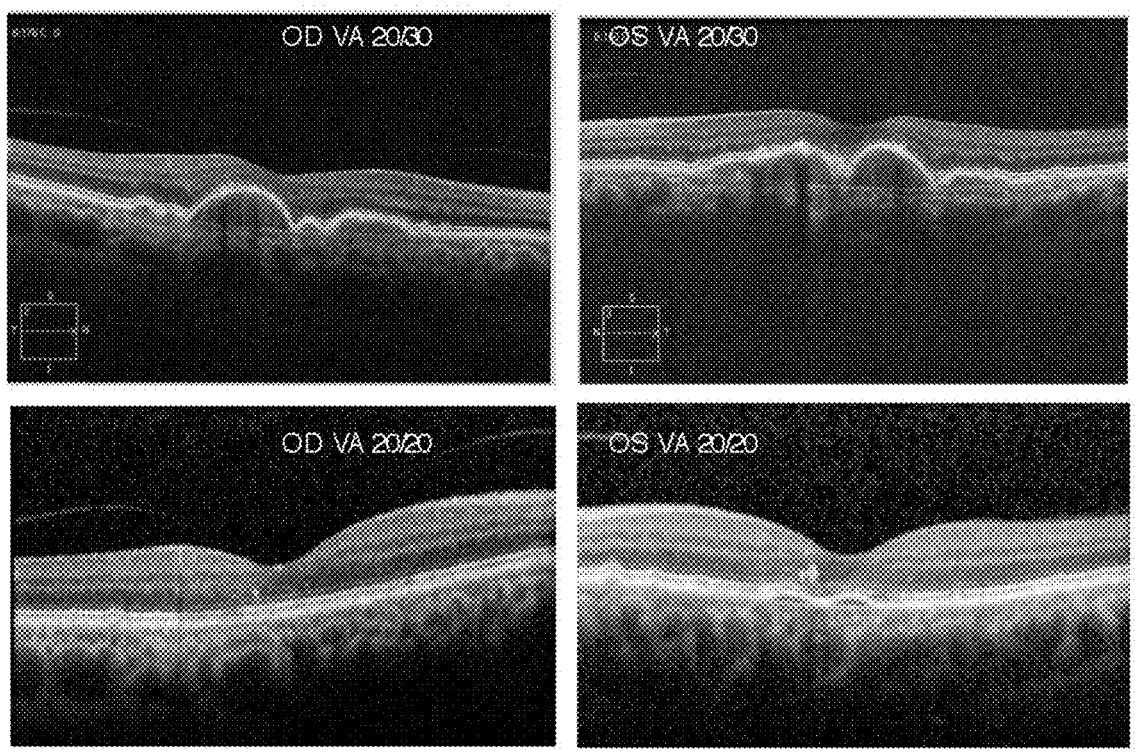
FIG. 2 is a spectral domain optical coherence tomography (SD-OCT). At the beginning of the trial overlying RPE and photoreceptor architectural distortion are seen (top row). After six months of 80 mg atorvastatin, complete disappearance of the drusen (FIG. 1) without accompanying atrophy of the RPE is seen (bottom row).

An otherwise healthy 63-year-old man with AMD presented deteriorating visual acuity. His baseline visual acuity was 20/25 with significant distortion; he was already taking Age-Related Eye Disease Study (AREDS) supplementation. Fundoscopy revealed bilateral extensive confluent large soft drusen and pigmentary alterations (FIG. 1, top row). Spectral domain optical coherence tomography (SD-OCT) confirmed the significant extent of these deposits and pigment epithelial detachments as well as the overlying RPE and photoreceptor architectural distortion (FIG. 2, top row). No subretinal or intraretinal fluid was present. Standard AREDS supplementation was continued. One year later, the patient became more symptomatic and VA was slightly decreased to as 20/30. The patient was started on atorvastatin, with gradual planned ramp up in dosage over 9 months from an initial 10 mg daily trial dose to the target 80 mg daily dose. Six months after 80 mg atorvastatin, visual acuity improved by 12 letters to 20/20, and examination with fundus examination and SD-OCT revealing complete disappearance of the drusen (FIG. 1) without accompanying atrophy of the RPE (FIG. 2).

Pilot Study

If 26 patients enrolled in the pilot study, 23 completed it. Three patients exited the study: one because of cramps, one because of muscle aches, and one because the patient felt the drug was inducing hair loss.

Ten of 23 patients (Table 1) responded to the treatment, and showed a regression of drusen deposits, with eight patients showing near-complete regression. On average, responders gained 3 letters whereas the non-responders lost 2.2 letters. The average time to response was 11.7 months (range 3-22). The average person-years of follow-up were ~30. None of the patients converted to neovascular AMD. According to an online risk calculator (available on the World Wide Web at caseyamdcalc.ohsu.edu based on Klein et al., 2011 Arch Ophthalmol. 129(12):1543-50), we should have expected 14% of our cases (3-4 out of the 23 patients) to convert to neovascular AMD.

TABLE 1

Characteristics of responders vs non-responders.

|  | All (n = 23) | Responders (n = 10) | Non Responders (n = 13) |  |
| --- | --- | --- | --- | --- |
| Age (years) | 68.1 +/− 6 | 70.6 +/− 6.2 | 66.2 +/− 5.5 | p = 0.08137 |
| Hypertension | 10 | 5/10 | 5/13 | Fisher 0.685018 |
| Initial Cholesterol | 208 +/− 34.9 | 210 +/− 33.4 | 207 +/− 37.4 | p = 0.859484 |
| Last Cholesterol | 147 +/− 31 | 161 +/− 34.2 | 136 +/− 24.4 | p = 0.057162 |
| Chol. Reduction | −62 +/− 35 | 49 +/− 31.2 | 71 +/− 35.9 | p = 0.140764 |
| Eye Vitamins | 14 | 7/10 | 7/13 | Fisher 0.669269 |
| Vitamin D use | 5 | 3/10 | 2/13 | Fisher 0.635117 |
| Fish oil Use | 5 | 2/10 | 3/13 | Fisher 1 |
| Aspirin use | 7 | 3/10 | 4/13 | Fisher 1 |
| Initial VA (Letters) | 77.6 +/− 8.3 | 74.2 +/− 9.9 | 80.2 +/− 6 | p = 0.089024 |
| Last VA (letters) | 77.7 +/− 8.4 | 77.5 +/− 10.3 | 77.9 +/− 7.1 | p = 0.908481 |
| VA gain (loss) |  | +3.3 | −2.3 | p = 0.061144 |

Responders were older than non-responders (70.6 vs. 66.2 median years of age) and had equal baseline cholesterol levels. Reduction of cholesterol levels did not appear to correlate with response status. There was a trend towards more multivitamin use and less alcohol consumption in responders, whereas there were no apparent differences in aspirin use, fish oil consumption, or anti-hypertensive medications. There were few smokers in our study, and thus we were not powered to assess the effect of smoking. High-dose atorvastatin did not appear to have a positive or negative effect on progression of pigmentary changes or of pre-existing atrophy.

Despite the high risk characteristics of our patient cohort, none of them progressed to neovascular or wet AMD.

Discussion

These results demonstrate that high-dose statin treatment can be used to treat high-risk features of dry AMD and prevent progression to atrophy or vision loss.

Example 2: Atorvastatin Promotes Phagocytosis and Attenuates Pro-Inflammatory Response in Human Retinal Pigment Epithelial Cells Methods and Materials Materials The human RPE cell line ARPE-19 was purchased from ATCC (Manassas, Va., US). DMEM/F-12, HEPES medium, fetal bovine serum (FBS) and penicillin-streptomycin were obtained from Life Technologies (Grand Island, N.Y., US). Recombinant human IL-1α was obtained from R&D Systems (Minneapolis, Minn., US). Cholesterol crystals were purchased from Sigma-Aldrich (St. Louis, Mo., US). Anti-IL-18 antibody, anti-IL-6 antibody, and anti-β-actin antibody were obtained from Abcam (Cambridge, Mass., US). Anti-IL-1β antibody and anti-IL-8 antibody were purchased from R&D Systems (Minneapolis, Minn., US). HRP-linked secondary antibodies were obtained from Cell Signaling Technology (Danvers, Mass., US).

Statins

Atorvastatin (atorvastatin calcium salt trihydrate), simavastatin and lovastatin (Mevinolin from *Aspergillus* sp.) were purchased from Sigma-Aldrich (St. Louis, Mo., US). They were reconstituted in dimethyl sulphoxide (DMSO; ATCC, Manassas, Va., US). A stock solution of 5 mM of each statin was prepared, and further dilutions were made in medium. Control cultures were incubated with DMSO at final concentrations corresponding to the highest concentrations added with the statins.

Cell Culture

ARPE-19 cells were maintained in DMEM/F-12, HEPES medium supplemented with 10% FBS, 100-U/mL penicillin, and 100-µg/mL streptomycin. The cells were grown in humidified 5% $CO_2$ at 37° C., and passaged when reaching 80% confluence.

Preparation of Cholesterol Crystals Solution

Cholesterol crystals were pulverized with a grinder and subsequently sterilized with UV light for 30 minutes. ARPE-19 culture medium was added to the cholesterol crystals to make a 6 mg/mL stock solution. The stock solution was sonicated until the cholesterol crystals were evenly suspended in the culture medium.

Preparation of Oxidized LDLs

LDLs (LEE Biosolution, Maryland Heights, Mo., US) were oxidized using $CuSO_4$ (Sigma, St. Louis, Mo., US), as described elsewhere (Hendriks et al., 1996 Biochem J 314 (Pt 2):563-8). Briefly, LDL (600 µl, 0.25 mg/ml), $CuSO_4$ (22.5 µl, 1.6 mM) and PBS (277.5 µl) were mixed and incubated at 37° C. The oxidation reaction was stopped using 1 mM of EDTA after 24 hours of incubation. Immediately after oxidation, lipoproteins were desalted using PD-10 disposable desalting columns (GE Healthcare, Buckinghamshire, UK).

Phagocytosis Analysis by Flow Cytometry

A flow cytometric assay was used to evaluate cell phagocytosis according to a protocol described by Pranab (Mukherjee et al., 2007 Proc Natl Acad Sci USA 104:13158-63). Briefly, ARPE-19 cells were seeded in 12-well plates and cultured until 90% confluent. Cells were incubated with $5 \times 10^7$/ml of 1 µm-diameter Fluoresbrite® YG Carboxylate Microspheres (Polysciences, PA, US) alone, or in combination with statin (atorvastatin, lovastatin or simvastatin), cholesterol crystals or ox-LDL; the concentrations of drugs used and exact duration of treatment are described for each experiment separately in the results section. After incubation, cells were washed with PBS three times to remove any extracellular beads, then trypsinized (0.25% trypsin-EDTA, Gibco, US) for 1 minute, and neutralized with pre-warmed culture medium. The cell suspension was collected and centrifuged (241 g, 5 minutes). The cell pellet was resuspended in 0.5 ml PBS for each sample. Subsequently, the cells were analyzed for green phagocytized fluorescent beads (excitation wavelength of 441 nm and emission wavelength of 486 nm) by a FACScalibur flow cytometer using the CellQuest 3.0.1 (Becton & Dickinson, Mountain View, Calif., US) and FlowJo 10.0 software. The percent of phagocytic cells present in each group was recorded as well as the mean fluorescence intensity of engulfed particles.

Fluorescence Recovery After Photobleaching (FRAP) to Assess Cell Membrane Fluidity ARPE-19 cells were cultured onto 35 mm glass bottom dishes (MatTek Corporation, MA) in DMEM/F12 medium supplemented with 10% FBS and 1% Penicillin/Streptomycin. 70-80% confluent cells were treated with 50 µM atorvastatin for 3 hours. Thirty minutes before measuring the membrane fluidity, cells were incubated with 5 µM of 4,4-difluoro-5,7-dimethyl-4-bora-3a,4a-diazas-indacene-3-dodecanoic acid (BODIPY® FL C12) (Thermo Fisher Scientific), a green fluorophore combined with a 12-carbon saturated hydrocarbon tail, dissolved in FluoroBrite™ DMEM medium (Thermo Fisher Scientific). Then, the cells were washed with FluoroBrite™ DMEM medium to remove any unincorporated dye, and were maintained at 37° C. and 5% $CO_2$ using an environmental chamber mounted on a microscope stage for FRAP measurements. FRAP measurements were made by photo-bleaching a microscopic area of the cell membrane (bleach Regions of Interest (ROIs) were drawn using a 7×7 pixel square) with a short (2 seconds), intensive pulse of light (458, 477, 488, and 514 nm lines simultaneously at 100% transmission) from an argon laser through a 63×, 1.4 numerical aperture oil immersion objective -with an additional 2× digital zoom (Total magnification=[10×][63×][2×]=1,260×)—of a Zeiss LSM 510 Axiovert 200M confocal laser scanning microscope. Recovery of fluorescence within the bleached area, due to lateral diffusion of neighboring intact fluorophore, was assessed by repetitive scanning across the cell surface (every 500 ms) with an attenuated laser beam (488 nm line at 3% transmission).

Western Blot

ARPE-19 cells were seeded in 6-well plates at a density of $1 \times 10^5$ cells/well. Twenty-four hours later, the cells were primed with IL-1α (5 ng/ml) for 8 hours, treated with atorvastatin (0.1, 0.5, or 5 µM) for 16 hours, and then incubated with either 2 mg/ml of cholesterol crystals for 6 hours, or 300 µg/ml oxLDL for 18 hours, with or without atorvastatin. After treatment, the culture medium was collected and centrifuged at 13.3 g for 15 minutes at 4° C. The supernatant was collected and stored at −80° C. Culture medium (for IL-6, IL-8) were loaded on each lane and the samples were run by electrophoresis. The proteins were transferred to a PVDF membrane and the membrane was blocked with non-fat milk and incubated with primary antibodies against IL-6 and IL-8. The membrane was then washed and incubated with secondary antibodies. The membrane was developed with enhanced chemiluminescence. The intensity of protein bands was measured using the software Image Lab 4.1 (Bio-Rad, Hercules, Calif., US).

Enzyme-Linked Immunosorbent Assay (ELISA)

IL-8 induced by oxLDL was measured by analysis of conditioned media of ARPE-19 cells using an ELISA kit (IL-8, R&D Systems, Minneapolis, Minn., US) according to the manufacturer's instructions.

Statistical Analysis

All experiments were performed in triplicate. Statistical analyses were performed using GraphPad Prism 5.0a. The results are expressed as mean±SE. The statistically significant difference between two-treatment groups was analyzed by unpaired t test. The value of $p<0.05$ was set as statistically significant.

Results

Lipophilic Statins Increase the Phagocytic Function of ARPE-19 Cells

To validate a method that reliably measures the phagocytic function of ARPE-19, cells were incubated with carboxylate microspheres for 6 hours, and then imaged using a confocal microscopy collecting a stack of 50 images. The cells were able to actively internalize the particles, which were located proximal to the nuclei (FIG. 3A-C), indicating that polystyrene microspheres can be phagocytized by ARPE-19 cells under these established conditions, and that this method can properly evaluate the phagocytic function of ARPE-19 cells.

Figure 3:
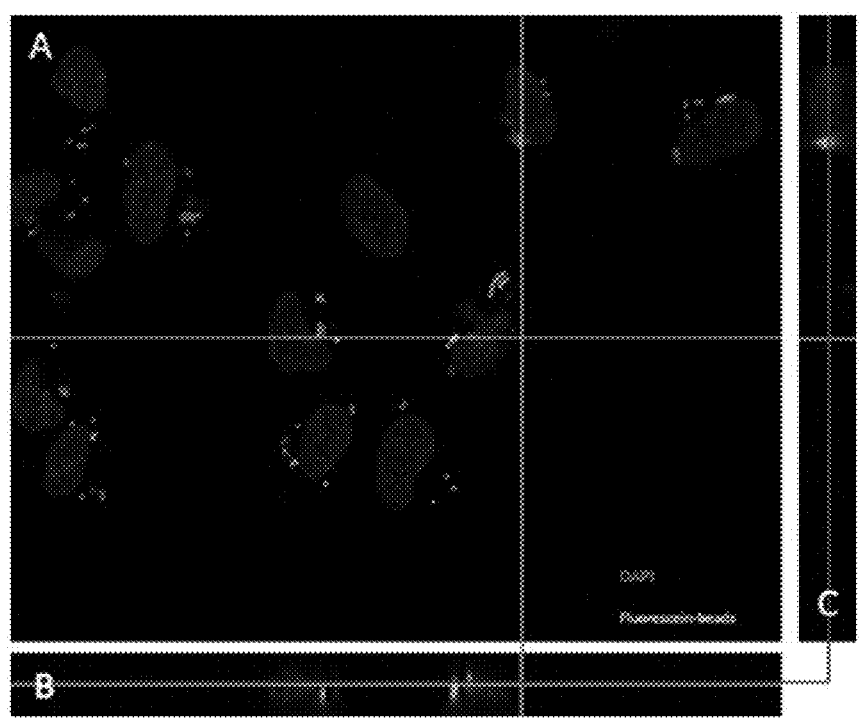
FIG. 3 shows that lipophilic statins increase the phagocytic function of ARPE-19 cells. (A-C) are microscopy images of ARPE-19 cells were incubated with carboxylate microspheres ($5 \times 10^7$ beads/ml) for 6 hours and then imaged using a confocal microscopy collecting a stack of 50 images. (A) A confocal image stack showing fluorescein-labeled beads and ARPE-19 cells with DAPI-labeled nuclei. The depth of image A within the stack is indicated by blue lines in B and C. (B) is a view through the same stack at the place denoted by the vertical line in A. (C) is a view through the same stack at the place denoted by the horizontal line in A. (D) is a graph showing a percent of phagocytic cells, represented by beads-positive cells or Y axis, and the phagocytic index, represented by fluorescence intensity or X axis, as determined by flow cytometry of ARPE-19 cells incubated with fluorescein-labeled carboxylate microspheres and treated for 6 hours with 50 µM of atorvastatin (ATV), lovastatin (LOV) or simvastatin (SIMV) (E) is a graph quantifying the percent of phagocytic cells. (F) is a graph quantifying the mean fluorescence intensity (or phagocytic index). Data is expressed as mean±SE. *p<0.05 versus control group.
Figure 3:
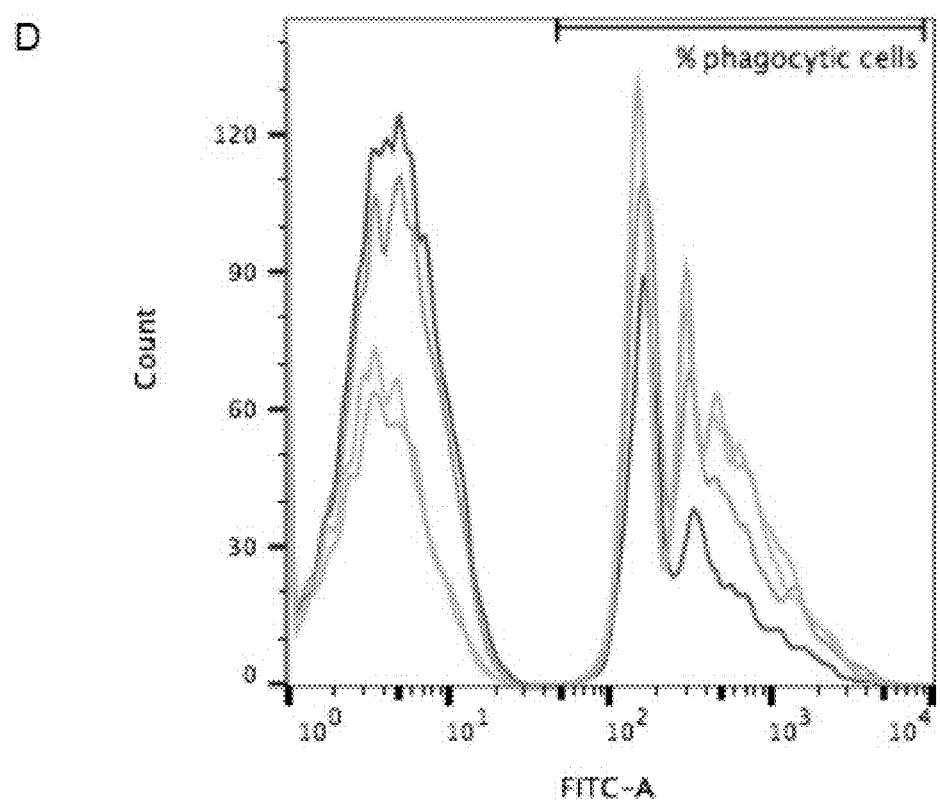
Figure 3:
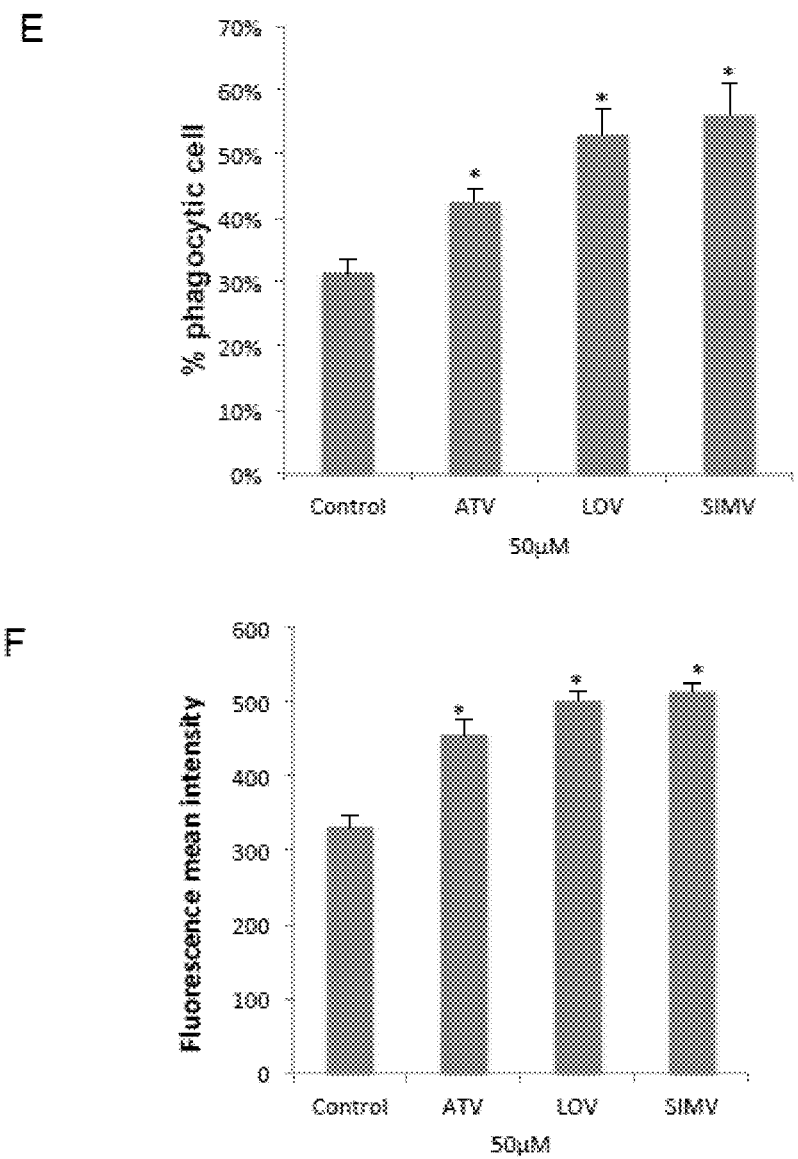

To investigate the effect of lipophilic, but not hydrophilic, statins on the phagocytic function of human RPE cells, ARPE-19 cells were incubated with polystyrene microspheres along with 50 µM of either atorvastatin, lovastatin, or simvastatin. The percentage of phagocytic ARPE-19 cells and the mean fluorescence intensity of engulfed particles per group were measured by flow cytometry 6 hours after treatment. As shown in FIGS. 3D and E, treatment with atorvastatin, lovastatin, or simvastatin significantly increased the percentage of ARPE-19 phagocytic cells from 31% to 43%, 53% and 56%, respectively ($p<0.05$). Similarly, an increase in the mean fluorescence intensity within ARPE-19 cells, from 332 to 455, 502 and 513, respectively ($p<0.05$) (FIG. 3F) was noted. This indicated that all three statins increased the phagocytic function of ARPE-19 cells, with simvastatin having the most potent effect, followed by lovastatin and atorvastatin.

Figure 4:
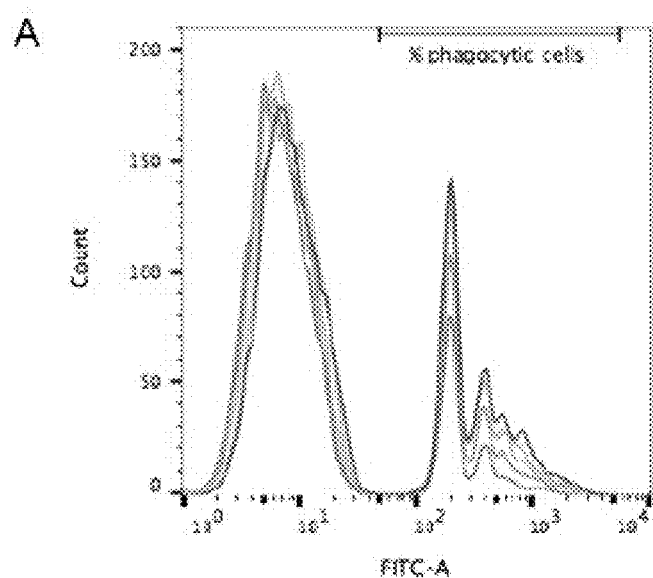
FIG. 4 contains graphs showing that atorvastatin increases the phagocytic function of ARPE-19 cells. (A) Percent of phagocytic cells, represented by beads-positive cells or Y axis, and the phagocytic index, represented by fluorescence intensity or X axis, as determined by flow cytometry of ARPE-19 cells incubated with fluorescein-labeled carboxylate microspheres and treated for 6 hours with 1, 25, 50, or 75 µM of atorvastatin (B) Quantification of the percent of phagocytic cells. (C) Quantification of the mean fluorescence intensity (or phagocytic index). Each experiment was repeated three independent times. Data is expressed as mean±SE. *p<0.05 versus control group.
Figure 4:
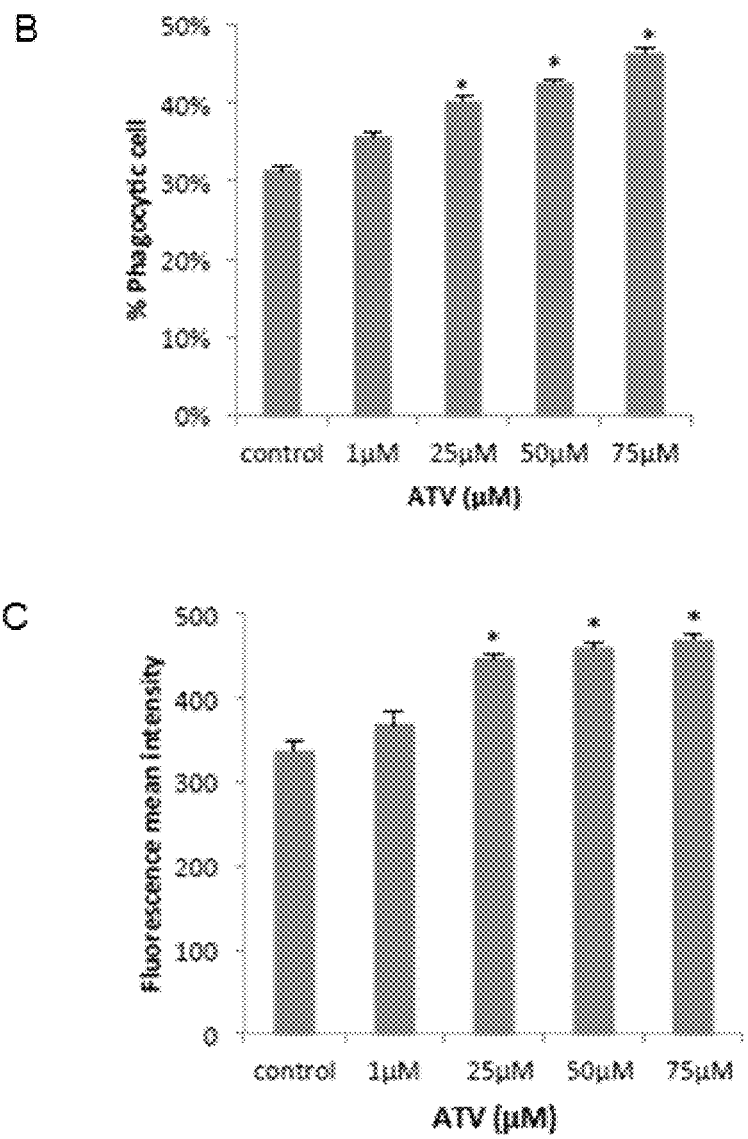

Atorvastatin Increases the Phagocytic Function of ARPE-19 Cells in a Dose-Dependent Manner High-dose atorvastatin resulted in regression of drusen deposits and improvement of visual acuity in select AMD patients (Example 1; Vavvas et al., 2016 *EBioMedicine* 5:198-203). To further explore the effects of high-dose atorvastatin on the phagocytic function of ARPE-9 cells, cells were incubated with both microspheres and different doses of atorvastatin for 6 hours, and the percentage of phagocytic RPE cells was evaluated by flow cytometry, as described previously. As shown in FIG. 4A and B, 1, 25, 50, or 75 µM of atorvastatin increased the percentage of phagocytic ARPE-19 cells to 35%, 40%, 42%, and 46%, respectively, compared to the baseline percentage (31%) of the DMSO control group ($p<0.05$). In addition, treating the cells with 1, 25, 50, or 75 µM of atorvastatin significantly increased the mean fluorescence intensity of cells from 340 in the control group to 368, 443, 453 and 467, respectively ($p<0.05$) (FIG. 4C). These data clearly indicate that atorvastatin increases the percentage of phagocytic cells and the phagocytic activity of ARPE-19 cells in a dose-dependent manner.

Atorvastatin Increases ARPE-19 Cell Membrane Fluidity

Figure 5:
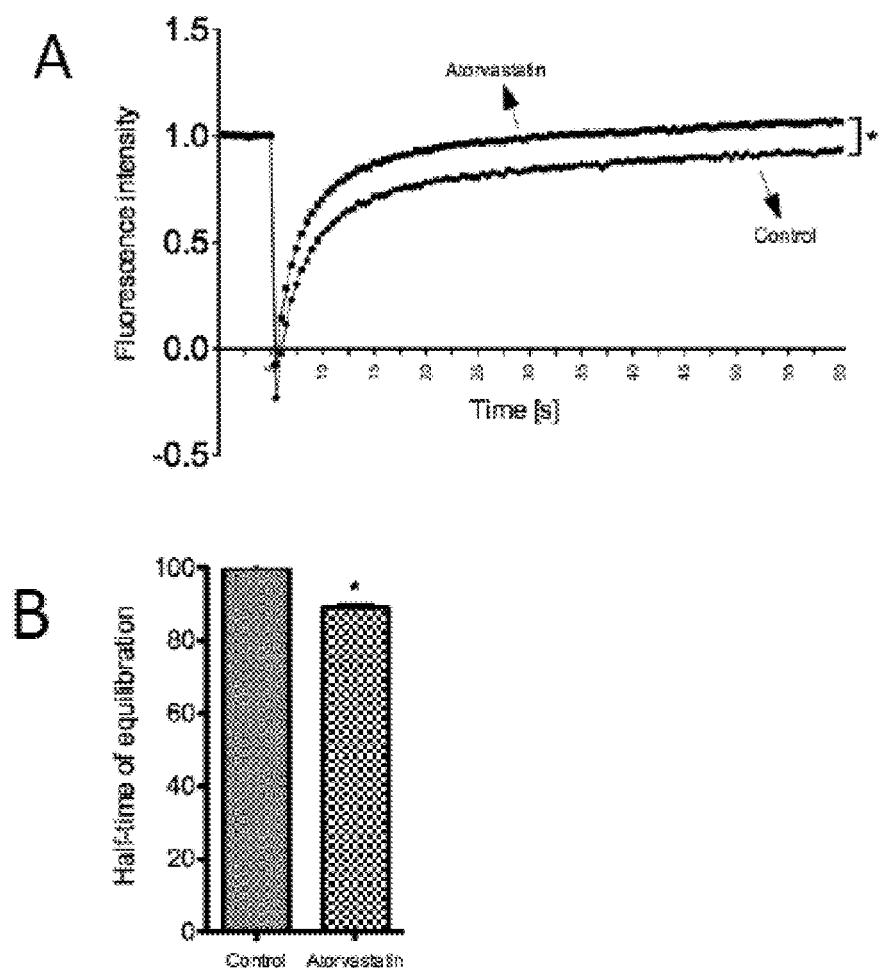
FIG. 5 contains graphs showing that atorvastatin increases the recovery of fluorescence in the membrane of ARPE19 cells after photo bleaching. FRAP measurements of ARPE-19 were done 3 hours after treatment with 50 µM atorvastatin with using the dye BODIPY® FL C12. (A) An average recovery curve of BODIPY® FL C12 in control (n=16 cells) or atorvastatin treated (n=16 cells) ARPE-19 cells from two independent experiments. (B) An average of normalized half-time of equilibration of BODIPY® FL C12 in control (n=16 cells) or atorvastatin treated (n=16 cells) ARPE19 cells from two independent experiments. Data is expressed as mean±SE. *p<0.05 versus control group.

To test the effect of atorvastatin on RPE cell membrane fluidity, ARPE-19 cells were incubated with 50 µM atorvastatin for 3 hours and BODIPY® FL C12 for 30 minutes. FRAP measurements were made by photo-bleaching a microscopic area of the cell membrane and the recovery of fluorescence within the bleached area was assessed by repetitive scanning across the cell surface with an attenuated laser beam, as described in the methods. Results showed that atorvastatin treatment increased the recovery of fluorescence in the membrane of ARPE19 cells after photo-bleaching (FIG. 5A). In addition, it decreased the half-time of fluorescence equilibration compared to the control group ($p<0.05$) (FIG. 5B). Both findings indicate that atorvastatin increases the membrane fluidity of ARPE-19 cells. This increase could, at least partially, explain the increase in phagocytic function of ARPE-19 cells after atorvastatin treatment.

Figure 6:
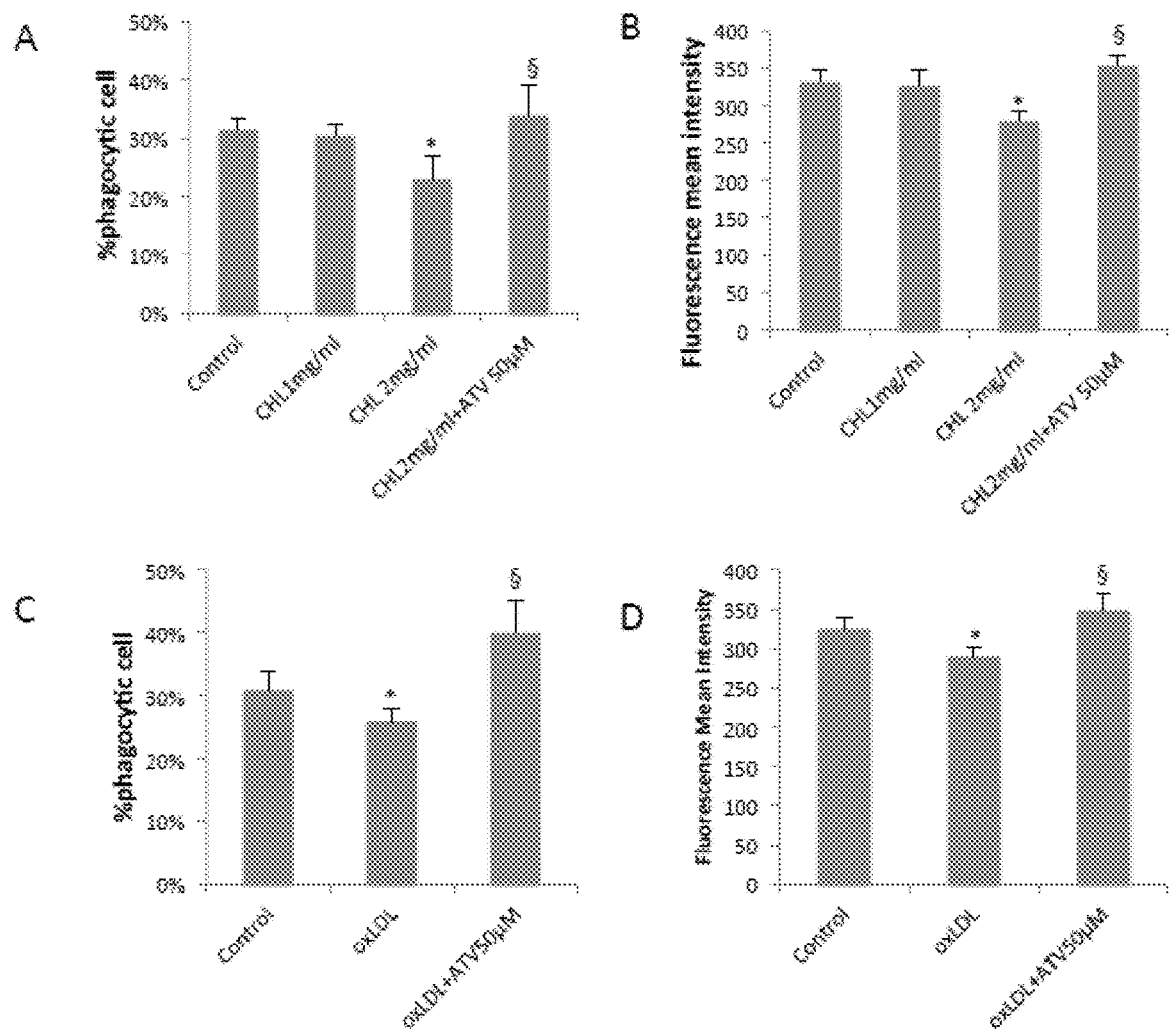
FIG. 6 is a series of graphs showing that atorvastatin restores the decreased phagocytic function induced by cholesterol crystals and ox-LDL in ARPE-19 cells. (A) ARPE-19 cells were incubated with carboxylate microspheres ($5 \times 10^7$ beads/ml), 1 or 2 mg/ml cholesterol crystals with or without 50 µM atorvastatin for 6 hours Quantification of the percent of phagocytic cells, represented by beads-positive cells, and (B) quantification of the mean fluorescence intensity (or phagocytic index) as determined by flow cytometry of ARPE-19 cells incubated with fluorescein-labeled carboxylate microspheres and treated for 6 hours with 1 or 2 mg/ml CHL with or without co-incubation with 50 µM of atorvastatin. (C) ARPE-19 cells were treated with 300 µg/ml ox-LDL for 18 hours then incubated with carboxylate microspheres ($5 \times 10^7$ beads/ml), with or without 50 µM atorvastatin for 6 hours. Quantification of the percent of phagocytic cells, represented by beads-positive cells, and (D) quantification of the mean fluorescence intensity (or phagocytic index) as determined by flow cytometry of ARPE-19 cells incubated with fluorescein-labeled carboxylate microspheres and treated for 18 hours with oxLDL with or without 50 µM of atorvastatin. Data is expressed as mean±SE. *p<0.05 versus control group. §p<0.05 versus 2 mg/ml CHL group or oxLDL group.

Atorvastatin Protects ARPE-19 Phagocytic Function from Impairment Induced by Cholesterol Crystals and ox-LDL The effects of cholesterol crystals and ox-LDL on the phagocytic function of RPE cells were studied because impairment of this function is linked to AMD (Nandrot et al., 2007 *Adv Exp Med Biol* 801:978-1). ARPE-19 cells were treated with 2 mg/ml cholesterol crystals for 6 hours, or 300 µg/ml oxLDL for 18 hours. The phagocytic function was then assessed by flow cytometry, as described in the methods. Cholesterol crystals significantly decreased the percentage of phagocytic cells from 31% to 22% ($p<0.05$) (FIG. 6A) and the mean fluorescence intensity of ARPE-19 cells from 332 to 280 ($p<0.05$) (FIG. 6B). Similarly, ox-LDL decreased the percentage of phagocytic cells from 31% to 26% ($p<0.05$) (FIG. 6C) and the mean fluorescence intensity of cells from 325 to 290 ($p<0.05$) (FIG. 6D).

Since atorvastatin increases the phagocytic function of ARPE-19, whether it could help preserve the phagocytic properties of these cells despite the impairment induced by cholesterol crystals and ox-LDL was checked. Pretreating the cells with 50 µM atorvastatin for 6 hours completely reversed the decrease in the percentage of phagocytic cells and mean fluorescence intensity induced by cholesterol crystals (FIGS. 6A and B) and ox-LDL (FIGS. 6C and D).

Taken together, these results suggest that atorvastatin protects the phagocytic function of ARPE-19 cells from the impairment induced by cholesterol crystals and ox-LDL.

Figure 7:
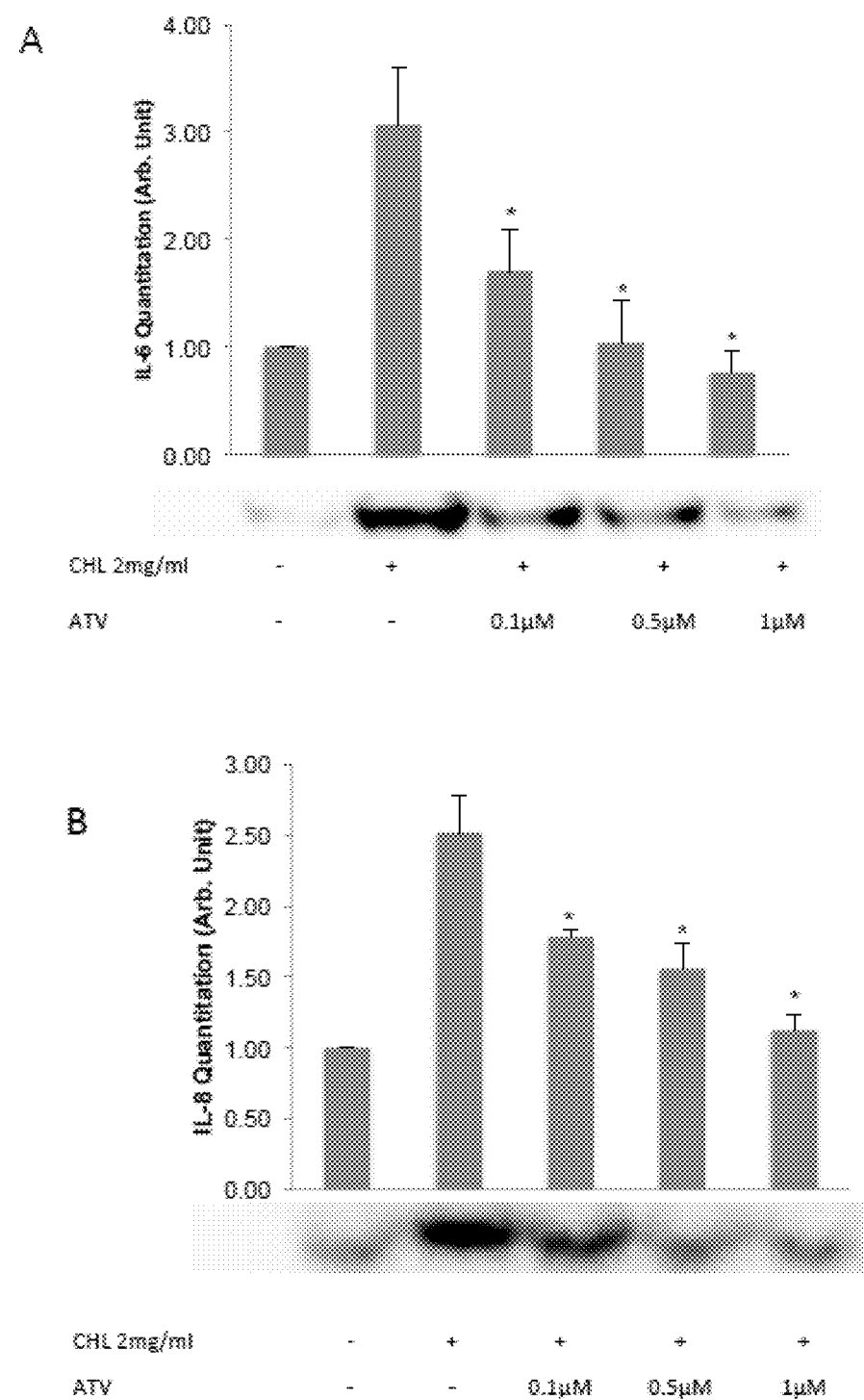
FIG. 7 is a series of graphs showing that atorvastatin inhibits IL-6 and IL-8 secretion induced by cholesterol crystals and oxLDL in ARPE-19 cells. IL-6 (A) and IL-8 (B) secretion from ARPE-19 cells as determined by western blot of culture medium 6 hours after CHL treatment with or without pre-treatment with 0.1, 0.5, or 1 µM of atorvastatin. IL-6 (C) and IL-8 (D) secretion from ARPE-19 cells as determined by western blot and ELISA respectively 18 hours after oxLDL treatment with or without pre-treatment with 0.1, 0.5, or 1 µM of atorvastatin. Data is expressed as mean±SE. *p<0.05 versus CHL treated group.
Figure 7:
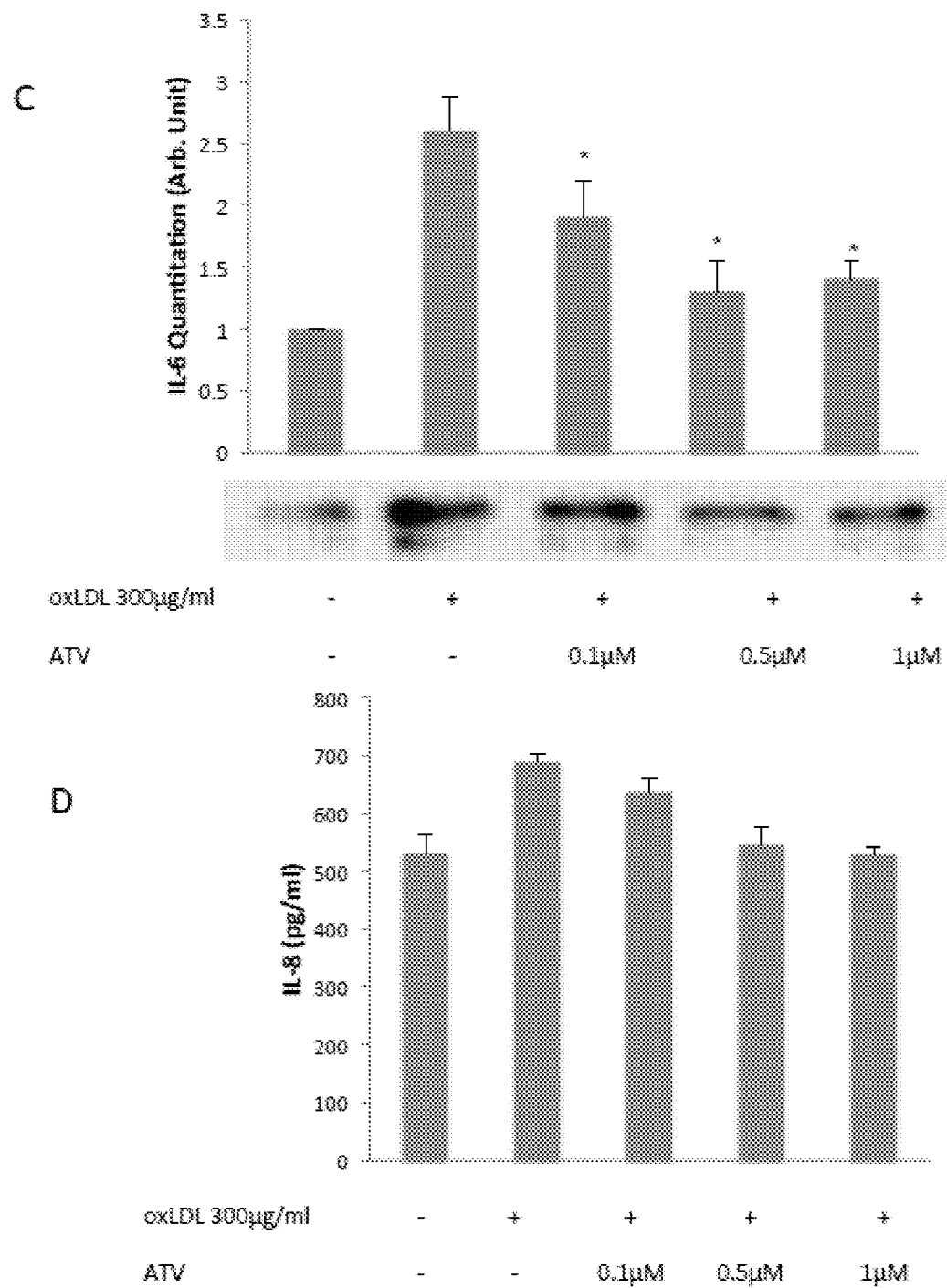

Atorvastatin Inhibits IL-6 and IL-8 Secretion induced by Cholesterol Crystals and ox-LDL in ARPE-19 Cells Cholesterol crystals induce the secretion of the inflammatory cytokines IL-6 and IL-8 in ARPE-19 cells (Hu et al., 2014 *Discovery Med.* 18(97):7-14). Since these cytokines are associated with the development and progression of AMD, whether atorvastatin can block this effect was investigated. ARPE-19 cells were primed with IL-1α, treated with different concentrations of atorvastatin, and then incubated with cholesterol crystals. The levels of IL-6 and IL-8 were evaluated using western blot or ELISA. As expected, cholesterol crystals increased ARPE-19 secretion of IL-6 and IL-8, 3.2- and 2.5-fold, respectively, compared to control treatment (FIGS. 7A and B). However, pretreating the cells with 0.1, 0.5 or 1 µM atorvastatin significantly reduced the levels of IL-6 to 1.7-, 1.-1 and 0.8-fold, respectively, and the levels of IL-8 to 1.8-, 1.6- and 1.1-fold, respectively, compared to control ($p<0.05$) (FIGS. 7A and B). In addition, we wanted to investigate the effect of ox-LDL on IL-6 and IL-8 in ARPE-19 cells and the effect of atorvastatin on the resulting consequences. Similar to cholesterol crystals, incubation of ARPE-19 with ox-LDL led to a 2.6- and 1.3-fold increase in secreted IL-6 and IL-8, respectively. However, pretreating the cells with 0.1, 0.5 or 1 µM atorvastatin was able to reduce the levels of IL-6 to 1.9-, 1.3- and 1.4- fold, respectively, and of IL-8 to 1.2-, 1.02- and 0.99-fold, respectively, compared to control ($p<0.05$) (FIGS. 7C and D). Both results indicate that atorvastatin can block, in a dose-dependent manner, the secretion of IL-6 and IL-8 induced by cholesterol crystals and ox-LDL in ARPE-19 cells.

Collectively, these data highly suggest that atorvastatin has an anti-inflammatory role in human RPE cells challenged with inflammatory inducers.

Discussion

Our study provides evidence that lipophilic statins enhance the phagocytic function of ARPE-19 cells, and that atorvastatin can protect these cells from the impairment of phagocytic function and the inflammatory effects induced by cholesterol crystals and ox-LDL. In addition, atorvastatin increases the membrane fluidity of ARPE-19 cells, which explains, at least partially, the positive effects of statins on the phagocytic function of these cells.

Since we used atorvastatin in our clinical study, we further focused on its in vitro effects on ARPE-19 cells. Interestingly, atorvastatin did not only increase the baseline phagocytic function of ARPE-19 cells, but also protected the cells against the phagocytic function impairment induced by cholesterol crystals and ox-LDL. This indicates that, in addition to playing a preventative role against AMD, the observed effect of atorvastatin on reversing the features of dry AMD can be partially explained by its ability to induce greater phagocytosis of existing drusen by RPE cells.

In summary, this study shows that the lipophilic statins atorvastatin, lovastatin and simvastatin have similar enhancing effects on the phagocytic function of ARPE-19 cells. It also shows that atorvastatin is an effective drug to protect ARPE-19 cells against the phagocytic impairment and the inflammatory effects induced by cholesterol crystals and ox-LDL. In addition, our study suggests the increase in cell membrane fluidity as an important mechanism for the observed effects of statins on the phagocytic function of ARPE-19. More importantly, our results introduce statins, a widely used and well-tolerated class of drugs with rare serious adverse effects, as a potentially effective medication for preventing and treating AMD.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of preventing progression to advanced age-related macular degeneration (AMD) in a patient with AMD, the method comprising administering to the patient a high-dose statin to: i) prevent progression to wet AMD; ii) prevent atrophy of a retinal pigment epithelium (RPE); iii) prevent atrophy of one or more photoreceptors; iv) prevent vision loss, or v) a combination of the foregoing,
wherein the high-dose statin is at least 40 mg atorvastatin per day, 0.4 mg cerivastatin per day, 120 mg fluvastatin per day, 90 mg lovastatin per day, 4 mg pitavastatin per day, 60 mg pravastatin per day, 20 mg rosuvastatin per day, or 60 mg simvastatin per day.

2. The method of claim 1 further comprising identifying the patient as having dry AMD and selecting the patient for treatment on the basis the patient has dry AMD.

3. The method of claim 1 further comprising identifying the patient as having AMD with high risk features for progression and selecting the patient for treatment on the basis the patient has high risk features for AMD progression.

4. The method of claim 1, further comprising monitoring the patient for efficacy of administering to the patient the high-dose statin.

5. The method of claim 4 further comprising monitoring the patient for progression to wet AMD, atrophy of the RPE, atrophy of one or more photoreceptors, or vision loss, wherein the monitoring comprises measuring a parameter indicative of progression to wet AMD, atrophy of the RPE, atrophy of one or more photoreceptors, or vision loss in the patient at a first time point prior to administration of the high-dose statin, measuring the same parameter in the patient at a second time point after administration of the high-dose statin, and comparing the parameter measured at the first time point and the second time point, wherein maintenance or reduction in the parameter from the first time point to the second time point indicates prevention of progression to wet AMD, prevention of atrophy of the RPE, prevention of atrophy of one or more photoreceptors, or prevention of vision loss.

6. The method of claim 4 further comprising monitoring the patient for visual acuity, wherein the monitoring comprises measuring a parameter indicative of visual acuity in the patient at a first time point prior to administration of the high-dose statin, measuring the same parameter in the patient at a second time point after administration of the high-dose statin, and comparing the parameter measured at the first time point and the second time point, wherein an increase in the parameter from the first time point to the second time point indicates improvement in visual acuity.

7. The method of claim 1, wherein the patient is a human.

8. The method of claim 1, wherein the high-dose statin is administered to the patient for at least 12 months, at least 15 months, at least 18 months, at least 21 months, at least 24 months, at least 30 months, at least 33 months, at least 36 months, at least 39 months, at least 42 months, at least 45 months, or at least 48 months.

9. The method of claim 1, wherein the high-dose statin is administered by a route selected from the group consisting of: i) intravenous administration; ii) ocular administration; iii) intramuscular administration; iv) subcutaneous administration; v) oral administration; vi) intranasal administration; vii) inhalation administration; viii) transdermal administration; ix) intravitreal administration; and x) parenteral administration.

10. The method of claim 1, wherein the high-dose statin is administered by an ocular route selected from the group consisting of: intravitreal, topical drops, and topical ointment.

11. The method of claim 1, wherein the statin is selected from the group consisting of atorvastatin, cerivastatin, fluvastatin, lovastatin, pitavastatin, pravastatin, rosuvastatin, simvastatin, and analogs thereof.

12. The method of claim 1, wherein the statin is a lipophilic statin.

13. The method of claim 12, wherein the lipophilic statin is selected from the group consisting of atorvastatin, lovastatin, simvastatin, and analogs thereof.

14. The method of claim 1, wherein the high-dose is a dose of the statin that exceeds the defined daily dose for the statin.

15. The method of claim 1, wherein the high-dose statin is at least 50 mg atorvastatin per day, 0.5 mg cerivastatin per day, 150 mg fluvastatin per day, 112.5 mg lovastatin per day, 5 mg pitavastatin per day, 75 mg pravastatin per day, 25 mg rosuvastatin per day, or 75 mg simvastatin per day.

16. The method of claim 1, wherein the high-dose statin is at least 60 mg atorvastatin per day, 0.6 mg cerivastatin per day, 180 mg fluvastatin per day, 135 mg lovastatin per day, 6 mg pitavastatin per day, 90 mg pravastatin per day, 30 mg rosuvastatin per day, or 90 mg simvastatin per day.

17. The method of claim 1, wherein the high-dose statin is at least 80 mg atorvastatin per day, 0.8 mg cerivastatin per day, 240 mg fluvastatin per day, 180 mg lovastatin per day, 8 mg pitavastatin per day, 120 mg pravastatin per day, 40 mg rosuvastatin per day, or 120 mg simvastatin per day.

18. The method of claim 1, further comprising administering to the patient a maintenance-dose statin after the patient has been administered the high-dose statin.

19. The method of claim 18, wherein the maintenance-dose statin administered per day is lower than the high-dose statin administered per day.

20. The method of claim 1, wherein administration is once a day, twice a day or three times a day.

21. The method of claim 1 further comprising administering to the patient an additional therapeutic agent, wherein the additional therapeutic agent is selected from the group consisting of an anti-inflammatory agent, an anti-angiogenic agent, an anti-oxidative agent, an omega-3 fatty acid, and a vitamin/mineral.

* * * * *